United States Patent [19]

Nevell et al.

[11] Patent Number: 5,637,280

[45] Date of Patent: Jun. 10, 1997

[54] STERILIZER

[75] Inventors: Vincent J. Nevell; Theresa M. Nevell, both of Coffs Harbour, Australia

[73] Assignee: Blixta Griffiths Pty. Limited c/o Econolodge, Sydney, Australia

[21] Appl. No.: 387,733

[22] PCT Filed: Aug. 16, 1993

[86] PCT No.: PCT/AU93/00418

§ 371 Date: May 26, 1995

§ 102(e) Date: May 26, 1995

[87] PCT Pub. No.: WO94/04198

PCT Pub. Date: Mar. 3, 1994

[30] Foreign Application Priority Data

Aug. 18, 1992 [AU] Australia ............... PL4197

[51] Int. Cl.⁶ ............................................. A61L 2/06
[52] U.S. Cl. ................. 422/299; 422/307; 219/430; 219/432; 219/434
[58] Field of Search ................. 422/295, 298, 422/299, 307; 219/430, 432–34, 439

[56] References Cited

U.S. PATENT DOCUMENTS

| | | | |
|---|---|---|---|
| 3,431,065 | 3/1969 | Schipanski | 422/298 X |
| 3,961,893 | 6/1976 | Russell et al. | 422/300 |
| 4,331,859 | 5/1982 | Thomas et al. | 422/307 X |
| 4,544,529 | 10/1985 | Hoeck | 422/298 X |
| 4,582,076 | 4/1986 | Prat | 422/307 X |
| 5,252,303 | 10/1993 | Goof | 422/299 X |

FOREIGN PATENT DOCUMENTS 2217629  1/1989  United Kingdom.

OTHER PUBLICATIONS

PCT/DK/88/00160; Int'l Publication No. WO89/02753; Publication Date 6 Apr. 1989 Patent Abridgment—Document No. AU-B-63649/90.

*Primary Examiner*—Robert J. Warden
*Assistant Examiner*—E. Leigh Dawson
*Attorney, Agent, or Firm*—Oppenheimer Poms Smith

[57] ABSTRACT

A sterilizer including a head and a detachable container sealingly engageable therewith to provide a pressure-resistant chamber. The head has a heating element mounted therein. The head is pivotably mounted to a frame such that the sterilizer may be selectively moved between a horizontal inoperative position and a vertical operative position with the container extending upwardly from the head. The water or sterilizer fluid are brought into contact with the heating element when the sterilizer is moved to the operative position so as to cause the fluid to vaporize and pressurize the chamber resulting in articles positioned in the chamber being sterilized.

8 Claims, 6 Drawing Sheets

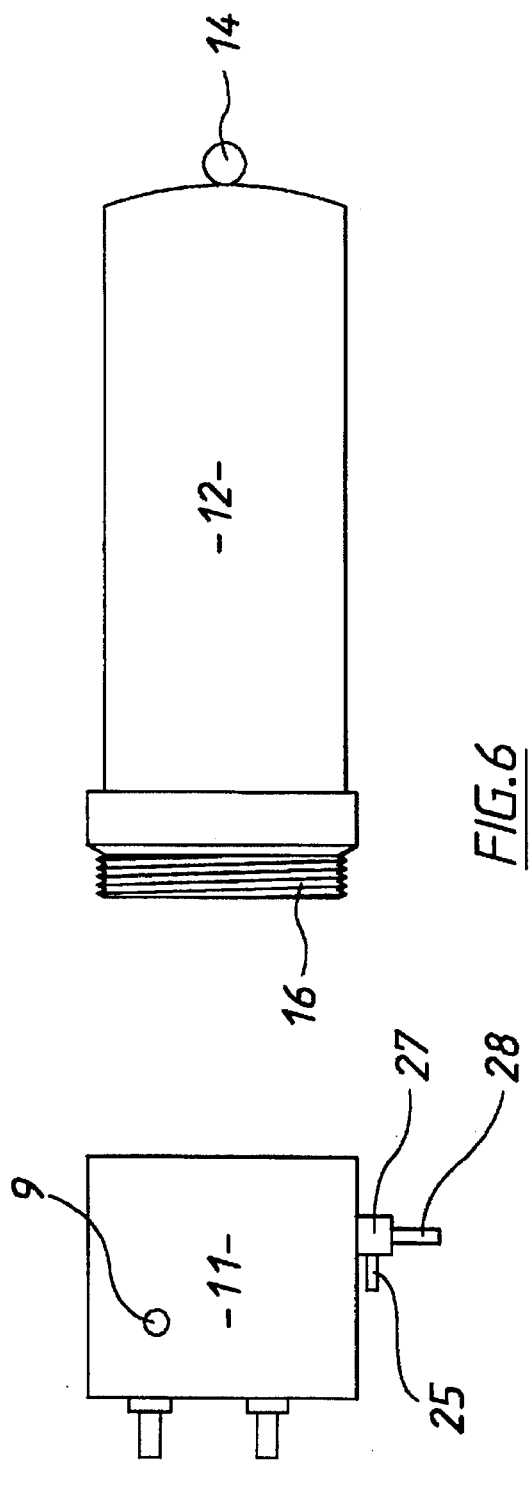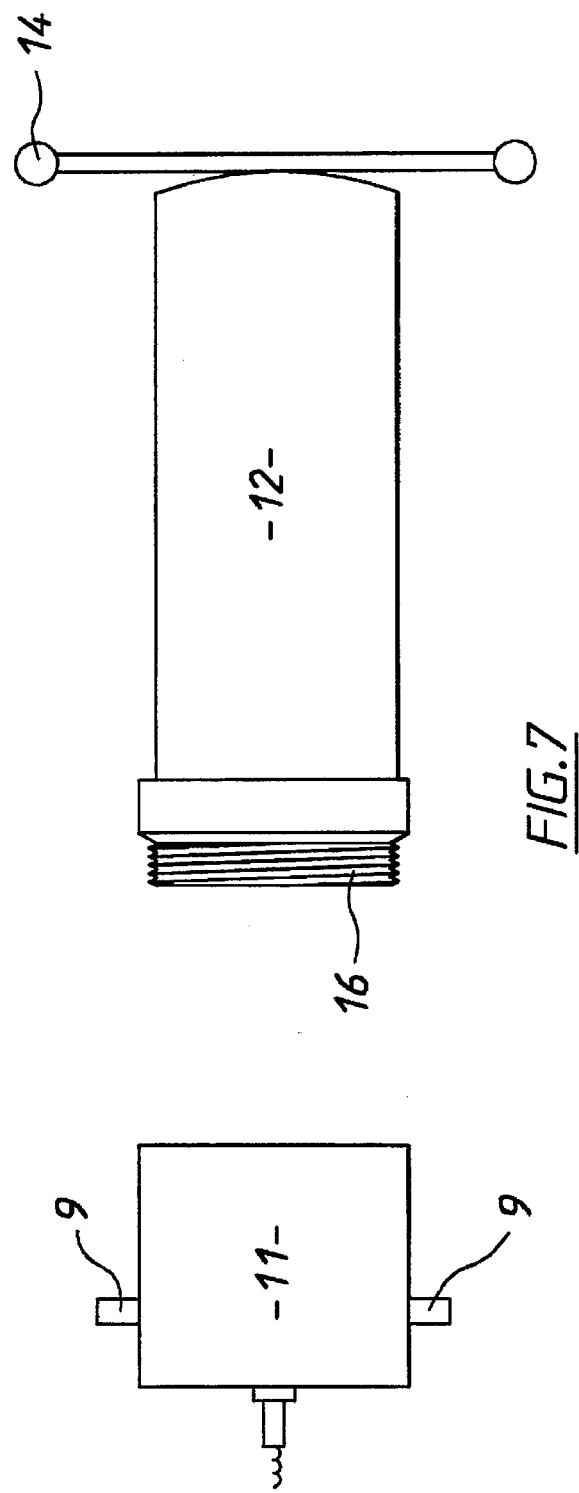

C
STERILIZER

TECHNICAL FIELD

The present invention relates to sterilisers, in particular, to instrument sterilisers used in dental surgeries.

BACKGROUND ART

At present dental instruments are sterilised by either boiling, autoclaving or chemical means. Autoclaving is generally accepted as the most effective means available. Chemical sterilisation is time consuming and reserved generally for items which will not survive autoclaving.

The real and imagined problems relating to the transmission of AIDS and hepatitis B have focussed attention on the dental handpiece which often only receives a quick wipe with alcohol. It is generally accepted that health authorities will in the near future require everything which is used in a patient's mouth to be autoclaved.

The high cost of dental handpieces makes it important to have a fast turnover through the autoclave. At present, a good autoclave cycles in about 12 minutes. Therefore, if a handpiece misses one cycle, it will not be ready for use for 24 minutes. Understandably, such a down-time would be unacceptable in most busy dental surgeries.

The present invention seeks to overcome these problems by providing a simple, inexpensive steriliser with a rapid cycle time.

DISCLOSURE OF THE INVENTION

According to the present invention there is provided a steriliser comprising a head and a detachable container sealingly engageable therewith to provide a pressure-resistant chamber, said head having mounted therein a heating means, control means coupled to said heating means for controlling the operation of the heating means to maintain its temperature within a predetermined range, heat sink means provided in the head surrounding the heating means, and means connected to the steriliser for bringing a predetermined volume of water or sterilising fluid into contact with the heating means and/or the heat sink means.

For preference, the head is provided with a controllable valve means communicating with said chamber to control the fluid pressure therein. In one particular preferred form the head is pivotally mounted to a frame such that the steriliser may be selectively moved between a horizontal inoperative position and a vertical operative position with the container extending upwardly from the head.

Preferably, the heating means is a thermostatically controlled electric heating element.

BRIEF DESCRIPTION OF THE DRAWINGS

A preferred embodiment of the invention will now be described, by way of example only, with reference to the accompanying drawings in which:

FIG. 6 shows a side elevation of the canister and head in a separated position;

FIG. 7 shows a plan view of the canister and head of FIG. 6;

BEST MODE FOR CARRYING OUT THE INVENTION

Figure 1:
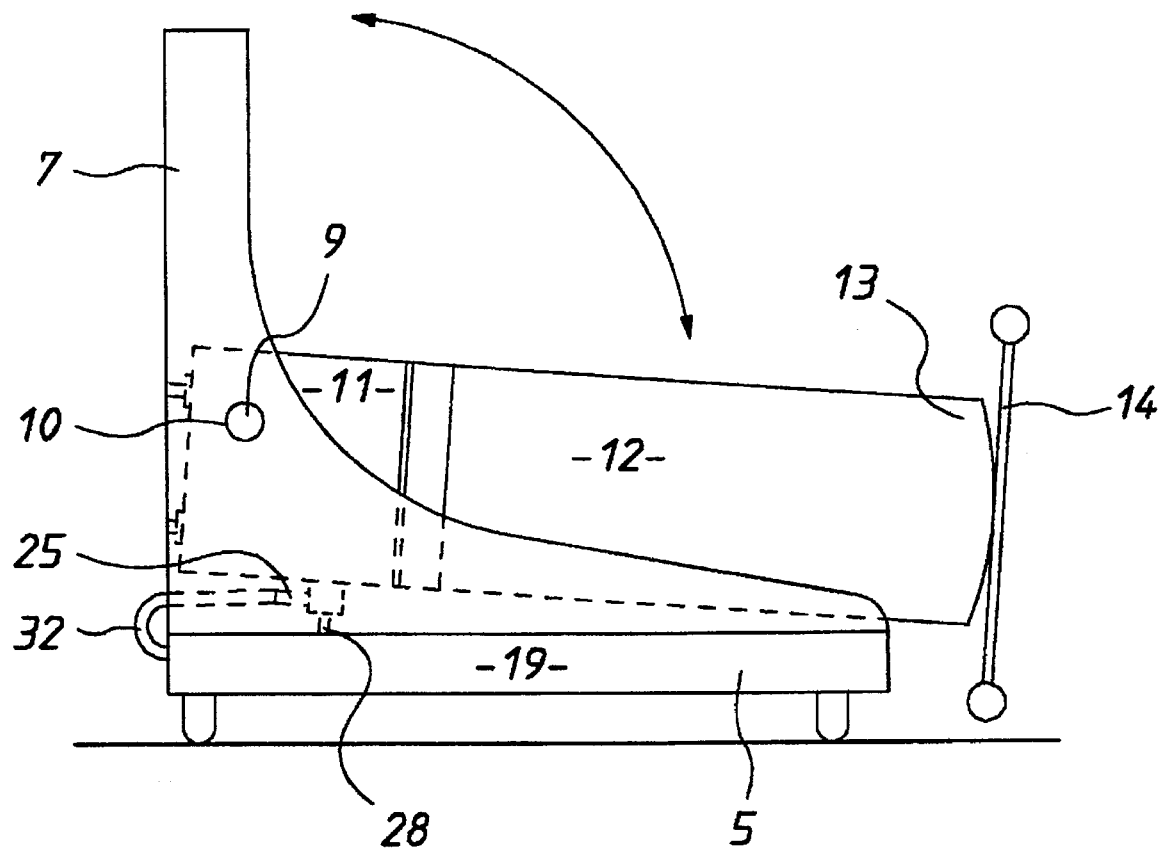
FIG. 1 shows a side elevation of the steriliser according to one embodiment of the invention.
Figure 2:
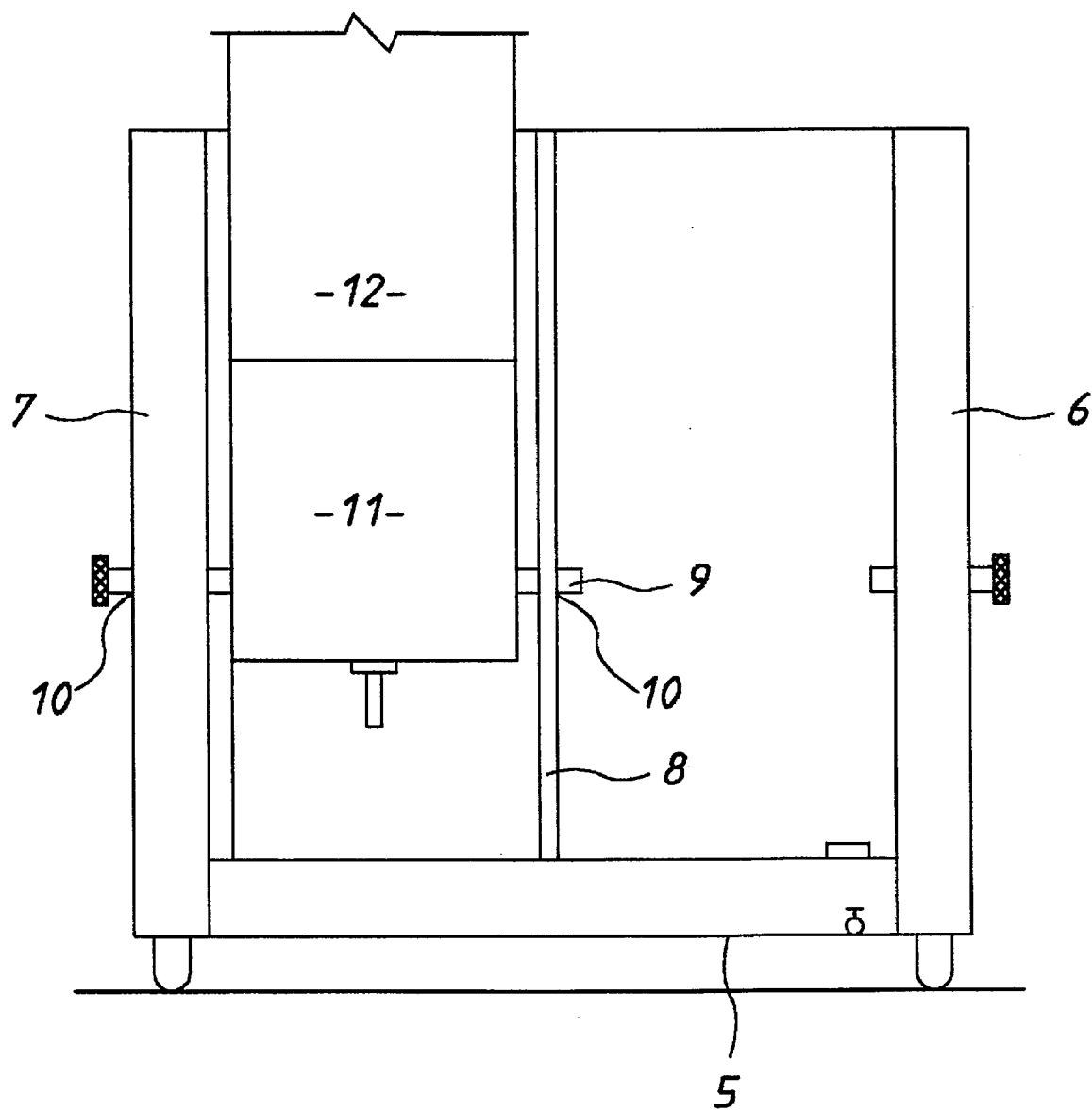
FIG. 2 shows an end elevation of the steriliser shown in FIG. 1.
Figure 3:
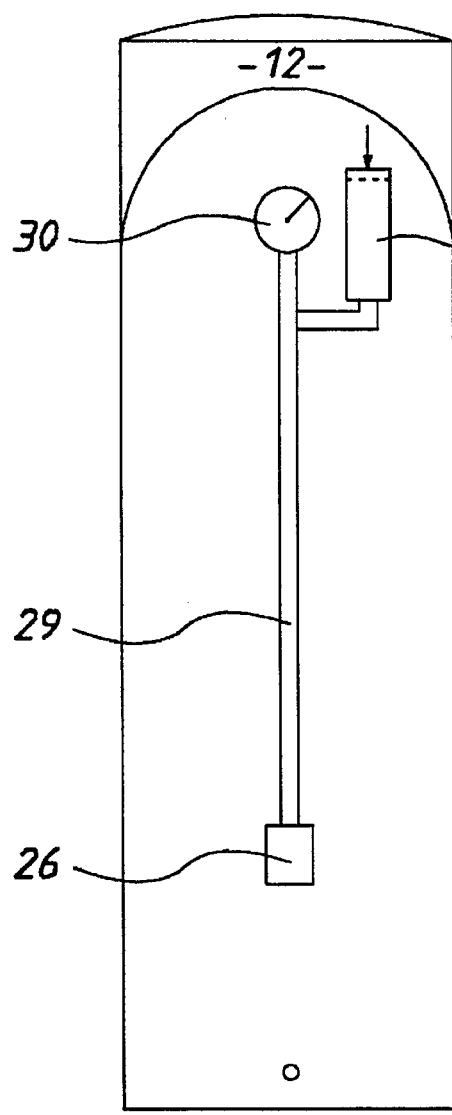
FIG. 3 shows an end elevation of the canister and head of FIG. 1 in the operative vertical position.
Figure 4:
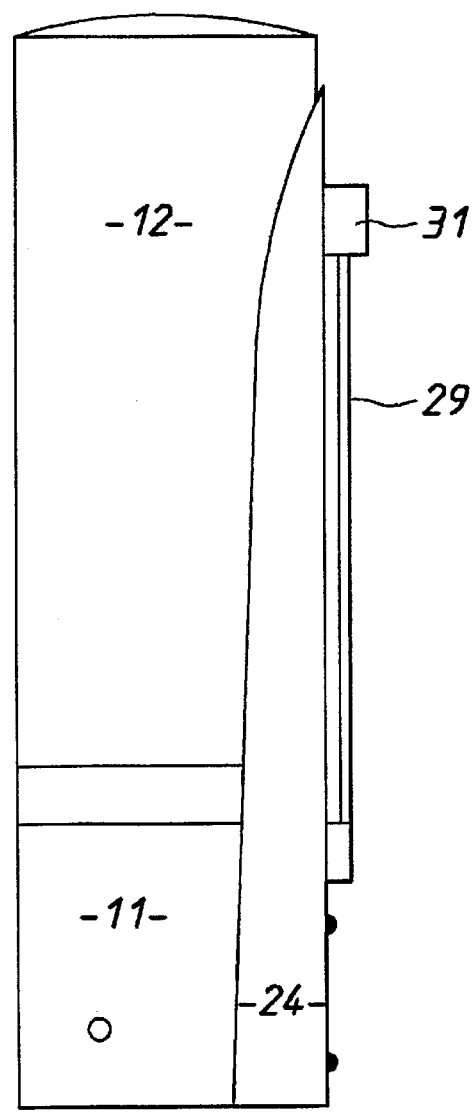
FIG. 4 shows a side elevation of the canister and head of FIG. 3.
Figure 5:
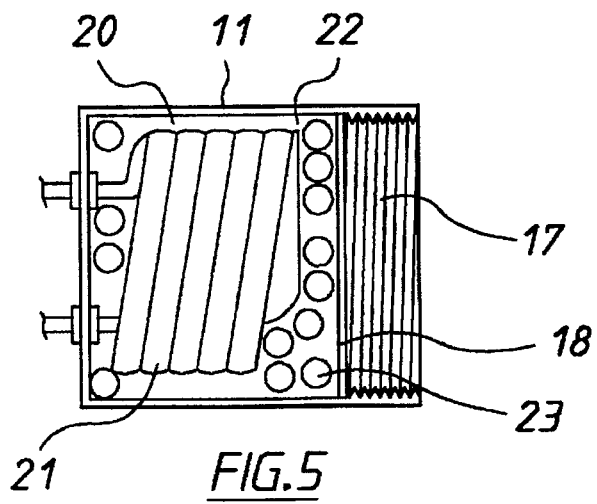
FIG. 5 shows a section view of the head of FIG. 3.

Referring to the drawings, a preferred embodiment of the invention will be now described. The steriliser comprises a base frame 5, having two side support frames 6 and 7 and a central support frame 8 extending vertically from the base frame 5. The support frames are journalled to receive a pivot axle 9 which passes through holes 10 in the support frames. The pivot axle 9 serves to pivot mount a head 11 of the steriliser to the base frame 5. The base frame shown accommodates two heads and it will be appreciated that the frame could be designed to accommodate any desired number of heads. The head 11 has screw mounted thereto an instrument receiving container 12 having at its end 13 remote from the screw mounting a handle 14 to assist fitting and removal of the container 12 from the head 11. The base frame 5 is further provided with an integral water tank and condenser 19.

Further details of the head and canister will be described with particular reference to FIGS. 3 to 7 of the accompanying drawings. The container 12 is in the form of a cylinder having one end closed and the other open to receive items to be sterilised. The open end 15 is provided with an external screw thread 16 for engaging an internal thread 17 provided in the opening of the head 11. A pressure seal 18 is provided in the head 11 to form a pressure tight seal when the container thread 16 is fully tightened into the head thread 17.

The head 11 is generally cylindrical in shape, having an internal cavity 20 into which is mounted a heating element 21. The heating element 21 is surrounded by a heat sink 22 which, in this embodiment, comprises a number of bronze balls 23 which are packed around the heating element 21. It will be appreciated that the heat sink can take other forms, such as metal rods, drilled solid bodies, granules of other suitable metals or the like. The container 12 is supported on a shaped support ramp 24 extending from the head 11. This ramp 24 assists in support and correct fitting of the container 12 to the head 11 when one is being screwed to the other. The head 11 is provided with two outlet ports 25 and 26. One of the ports 25 has a pressure relief valve 27 operable by control button 28 for selectively opening the port 25. The other port 26 is connected by a tube 29 to a pressure gauge 30 and safety relief valve 31 mounted on the underside of the support ramp 24. The port 25 is connected by a flexible tube 32 to a condenser coil (not shown) positioned in the water tank 19.

In use, the heating element 21 is maintained in a preselected temperature range by a thermostatic control of the electric current feed to the element 21. The element 21 may also be controlled by a pressure switch which deactivates the element when a desired pressure is reached within the head. The element remains on throughout the day with heat loss limited by a cap which may be fitted to the head in the absence of the container. The element cycles within a preset temperature range.

To sterilise an item, the canister 10 is unscrewed from the head 11 and the item to be sterilised placed in the container 12 with a predetermined amount of water. The container 12 is then screwed into the head 11 while resting in a generally horizontal position as shown in FIG. 1. The container 12 is then pivotted about the axle 9 to a vertical position causing the water to contact the heating element 21 and heat sink 22 resulting in the production of steam, pressure and temperature within the container 12. The pressure being controlled by the pressure release valve or the safety valve 26. Once the autoclaving has been completed, the container is lowered to the horizontal position which activates the pressure relief valve on the head via control button 28, resulting in the internal pressure being totally released and the steam passing into the condenser coil via tube 32. The sterilised item may then be removed by unscrewing the container 12.

Figure 8:
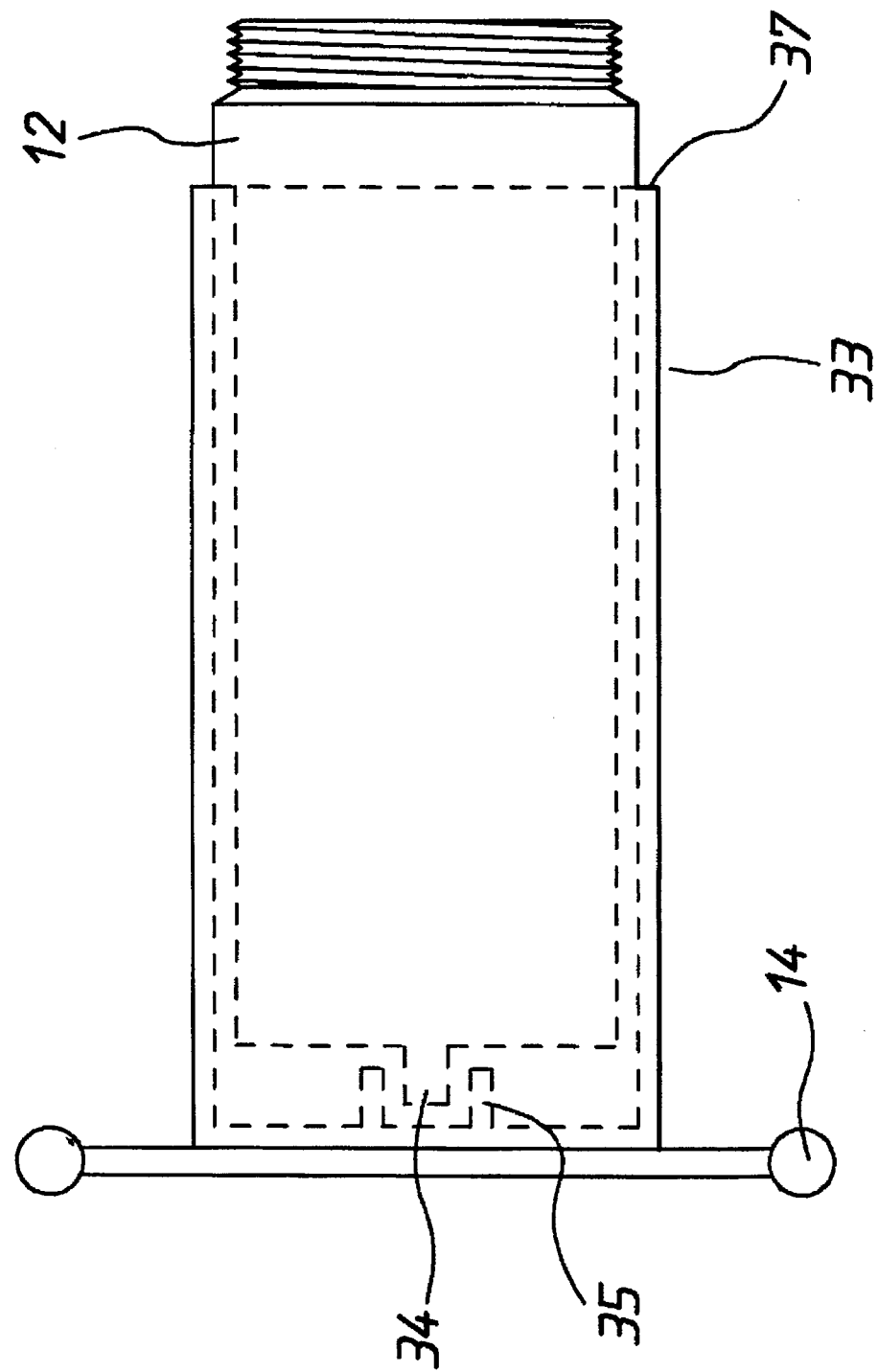
FIG. 8 shows a side elevation of a further embodiment of the canister arrangement according to the invention.
Figure 9:
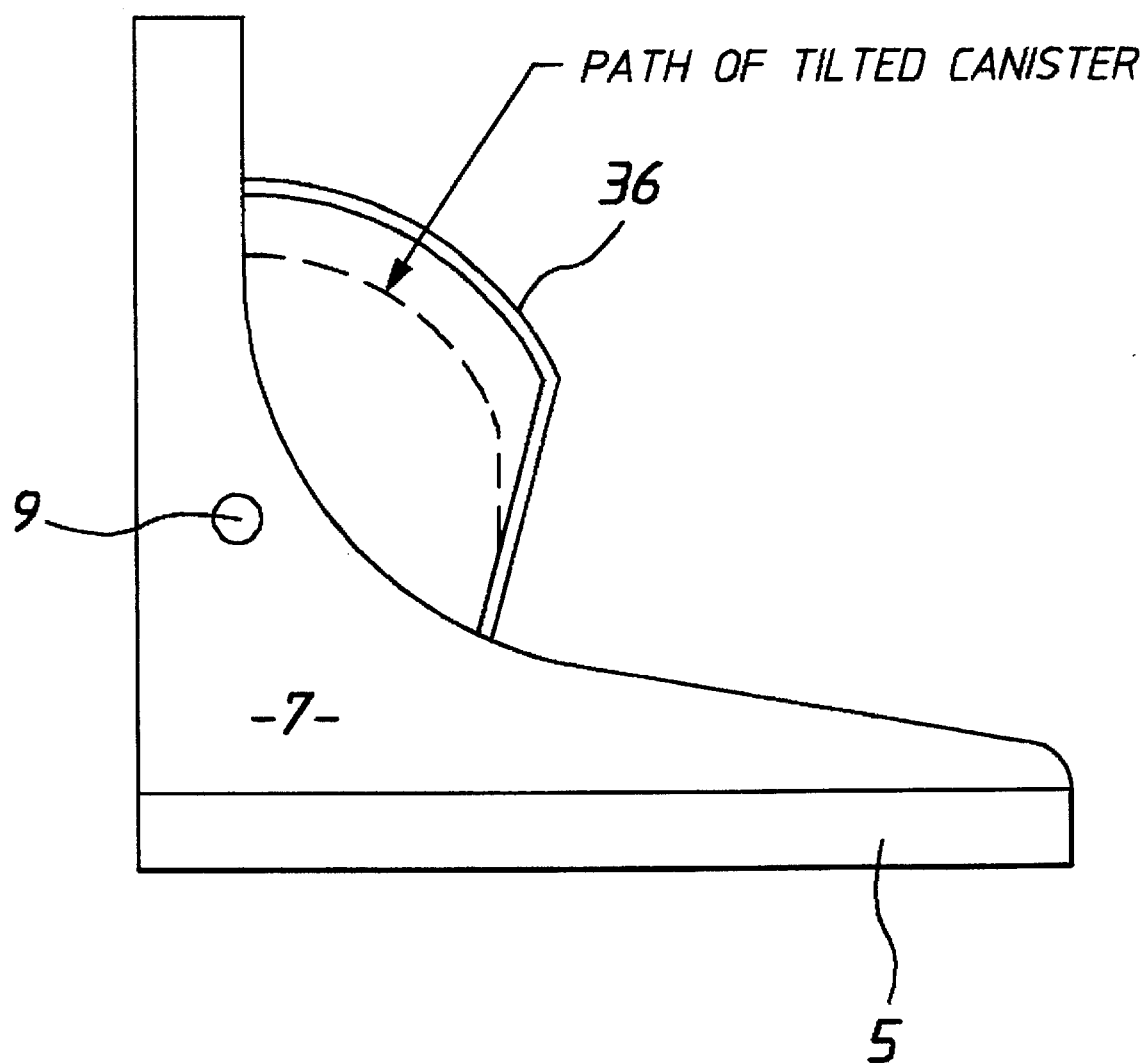
FIG. 9 shows a side elevation of the support used for the canister arrangement of FIG. 8.

In a further preferred form of the invention shown in FIGS. 8 and 9, the container 12 is surrounded by a sleeve 33. The closed end of the container 12 is provided with a shaped protrusion or boss 34 which engages with a complementary shaped recess 35 on the inner side of the closed end of the sleeve 33. When engaged the boss 34 and recess 35 prevent relative rotational movement between the sleeve 33 and the container 12 so that the handle 14 on the sleeve 33 may be used to screw the canister 12 into engagement with the head 11. The sleeve 33 fits over the container 12 with a small air gap and serves to insulate the container 12 against heat loss or burns and to act as a handle for the container 12.

To prevent unintentional opening of the canister 12 during operation, the frame 5 is provided with a guide rail 36 which engages with the outer edge 37 of the open end of the sleeve 33 and acts to slide the sleeve 33 and its associated boss 34 out of engagement with the recess 35 as the container is raised to its operative position. This disengagement of the sleeve from the container prevents unintentional opening of the container during the sterilising operation.

It will be appreciated that water or sterilising fluid may be introduced into contact with the heating element by any suitable means, for example the head could remain in a fixed position and fluid could be injected into contact with the heating element using a pump. Alternately, the head may be provided with a fluid reservoir having a spring-loaded push valve connecting the reservoir to the interior of the head. A screw cap on the reservoir, on being tightened, depresses the push valve to cause fluid to enter the head and contact the heating element. The valve closes automatically under force of the internal pressure and the spring.

It will be further appreciated that other embodiments of the invention are possible without departing from the spirit or scope of the invention described and the invention is not limited to the specific embodiment described or in its application to dental instruments.

We claim:

1. A steriliser for use with fluids including water and sterilising fluid, the steriliser comprising:
    a head having a heating element mounted therein;
    a container associated with the head, the head and container together defining a pressure-resistant chamber;
    a heat sink associated with the head and in heat transferring proximity to the heating element;
    a controller operably connected to the heating element and adapted to maintain the heating element at temperatures within a predetermined temperature range corresponding to the production of steam by at least one of the heating element and the heat sink; and
    a frame and an axle associated with the frame upon which the pressure-resistant chamber is pivotally mounted such that the pressure-resistant chamber may be selectively moved between a substantially horizontal inoperative position where a predetermined volume of fluid within the container does not come into contact with the heating element and the heat sink and a substantially vertical operative position with the container extending upwardly from the head where the fluid contacts at least one of the heating element and the heat sink.

2. A steriliser as claimed in claim 1, wherein the head includes a controllable valve operably connected to the chamber for controlling fluid pressure in the chamber.

3. A steriliser as claimed in claim 1, wherein the head and container define separate structural elements, the steriliser further comprising:
    connection means for connecting the head to the container; and
    safety means for preventing separation of the container and the head when the steriliser is in the operative position.

4. A steriliser for use with fluids including water and sterilising fluid, the steriliser comprising:
    a head having a heating element mounted therein and a container associated with the head, the head and container together defining a pressure-resistant chamber;
    a controllable valve associated with the head and operably connected to the chamber for controlling fluid pressure in the chamber by substantially releasing the fluid pressure in the chamber in response to a movement of the pressure-resistant chamber from an operative position to an inoperative position;
    a heat sink associated with the head and in heat transferring proximity to the heating element;
    a controller operably connected to the heating element and adapted to maintain the heating element at temperatures within a predetermined temperature range corresponding to the production of steam by at least one of the heating element and the heat sink; and
    fluid control means, associated with the pressure-resistant chamber, for allowing a predetermined volume of fluid to be transferred from a first location, where the fluid does not come into contact with the heating element and the heat sink, to a second location where the fluid contacts at least one of the heating element and the heat sink.

5. A steriliser as claimed in claim 4, further comprising:
    a condenser operably connected to the controllable valve for condensing fluid released from the chamber.

6. A steriliser for use with fluids including water and sterilising fluid, the steriliser comprising:
    a head having a heating element mounted therein;
    a container associated with the head, the head and container defining separate structural elements and together defining a pressure-resistant chamber;
    complimentary screw threads on the head and container for connecting the head to the container;
    an outer sleeve surrounding the container and selectively engagable therewith such that separation of the container and the head is prevented when the steriliser is in an operative position, the outer sleeve being engaged with the container when the steriliser is in the inoperative position, thereby allowing the container to be rotated by the outer sleeve and removed from the head;
    a heat sink associated with the head and in heat transferring proximity to the heating element;
    a controller operably connected to the heating element and adapted to maintain the heating element at temperatures within a predetermined temperature range corresponding to the production of steam by at least one of the heating element and the heat sink; and fluid control means, associated with the pressure-resistant chamber, for allowing a predetermined volume of fluid to be transferred from a first location, where the fluid does not come into contact with the heating element and the heat sink, to a second location where the fluid contacts at least one of the heating element and the heat sink.

7. A steriliser as claimed in claim 6, further comprising:

means for disengaging the outer sleeve from the container, thereby allowing the outer sleeve to move freely relative to the container when the steriliser is in the operative position.

8. A steriliser for use with fluids including water and sterilising fluid, the steriliser comprising:

a head having a heating arrangement mounted therein;

a container associated with the head, the head and container together defining a chamber;

a controller operably connected to the heating arrangement and adapted to maintain the heating arrangement at temperatures within a predetermined temperature range corresponding to the production of steam by the heating arrangement;

a frame; and an axle associated with the frame, the chamber being pivotally mounted on the frame by the axle such that the chamber may be selectively moved between a substantially horizontal inoperative position and a substantially vertical operative position with the container extending upwardly from the head.

* * * * *